United States Patent
Nad et al.

(10) Patent No.: US 12,391,905 B2
(45) Date of Patent: Aug. 19, 2025

(54) NON-SOAP DETERGENT BAR COMPOSITIONS

(71) Applicants: Dow Global Technologies LLC, Midland, MI (US); Dow Silicones Corporation, Midland, MI (US)

(72) Inventors: Saugata Nad, Brussels (BE); Padmadas Nair, Maharashtra (IN); Priti Jain, Mumbai (IN); Amit Kumar Verma, Uttar Pradesh (IN)

(73) Assignees: Dow Global Technologies LLC, Midland, MI (US); Dow Silicones Corporation, Midland, MI (US)

( * ) Notice: Subject to any disclaimer, the term of this patent is extended or adjusted under 35 U.S.C. 154(b) by 242 days.

(21) Appl. No.: 18/015,812

(22) PCT Filed: Aug. 20, 2021

(86) PCT No.: PCT/US2021/046808
§ 371 (c)(1),
(2) Date: Jan. 12, 2023

(87) PCT Pub. No.: WO2022/040488
PCT Pub. Date: Feb. 24, 2022

(65) Prior Publication Data
US 2023/0257684 A1     Aug. 17, 2023

(30) Foreign Application Priority Data
Aug. 21, 2020  (IN) .............. 202041036063

(51) Int. Cl.
*C11D 17/00* (2006.01)
*C11D 1/22* (2006.01)
*C11D 3/08* (2006.01)
*C11D 3/10* (2006.01)
*C11D 3/12* (2006.01)
*C11D 3/22* (2006.01)
*C11D 3/382* (2006.01)

(52) U.S. Cl.
CPC ............ *C11D 17/0069* (2013.01); *C11D 1/22* (2013.01); *C11D 3/08* (2013.01); *C11D 3/10* (2013.01); *C11D 3/222* (2013.01); *C11D 3/382* (2013.01)

(58) Field of Classification Search
None
See application file for complete search history.

(56) References Cited

U.S. PATENT DOCUMENTS

| 4,692,275 A * | 9/1987 | Secemski ................ C11D 1/37 510/498 |
| 5,703,026 A | 12/1997 | Setser et al. |
| 6,251,843 B1 | 6/2001 | Chambers et al. |
| 2007/0155639 A1 | 7/2007 | Salvador et al. |
| 2011/0028373 A1* | 2/2011 | Fossum .................. C11D 17/00 510/236 |
| 2011/0183881 A1 | 7/2011 | Delos Reyes |
| 2015/0291919 A1* | 10/2015 | Jones ...................... A61K 8/11 510/130 |
| 2018/0154328 A1* | 6/2018 | Ferguson ............... C11D 3/222 |

FOREIGN PATENT DOCUMENTS

| EP | 2319909 | 5/2011 | |
| GB | 2177717 A * | 1/1987 | ........... C07C 309/00 |
| GB | 2276630 | 10/1994 | |
| WO | 1998018896 | 5/1998 | |
| WO | 2000040691 | 7/2000 | |
| WO | WO-0107554 A1 * | 2/2001 | ......... C11D 11/0017 |
| WO | WO-0142413 A1 * | 6/2001 | ........... C11D 17/006 |
| WO | 2002046346 | 6/2002 | |
| WO | WO-2011020679 A1 * | 2/2011 | ............. C11D 3/126 |

OTHER PUBLICATIONS

Sibilia, "A Guide to Materials Characterization and Chemical Analysis", VCH, 1988, pp. 81-84.
Yau, "Modem Size Exclusion Chromatography", Wiley-Interscience, 1979.

* cited by examiner

Primary Examiner — Lorna M Douyon
(74) Attorney, Agent, or Firm — Thomas S. Deibert

(57) ABSTRACT

A non-soap detergent bar is provided, comprising: a detergent surfactant; a builder; a psyllium; a cellulose derivative; a filler, wherein the filler includes sodium silicate; and water; wherein the non-soap detergent bar is a solid.

20 Claims, No Drawings

NON-SOAP DETERGENT BAR COMPOSITIONS

The present invention relates to a non-soap detergent bar. In particular, the present invention relates to a non-soap detergent bar, comprising: a detergent surfactant; a builder; a psyllium; a cellulose derivative; a filler, wherein the filler includes sodium silicate; and water; wherein the non-soap detergent bar is a solid.

Bar soaps remain popular with consumers for cleansing laundry, hard surfaces and skin.

Laundry detergent bars are used in many locales for cleaning clothes. Technical developments in the field of laundry detergent bars have involved the formulation of laundry detergent bars which are effective in cleaning clothes; have acceptable sudsing characteristics in warm and cool water, and in both hard and softwater; and also have acceptable in-use wear rates, hardness, durability, feel, have low slough and rapid drying.

Sodium tri-polyphosphate (STPP) has conventionally been considered to be a good builder and structurant for laundry bars. It helps to provide good binding of the bars and promotes longer wear times. It also contributes to alkalinity, anti-redeposition and cleaning efficiency of bars. Notwithstanding, high concentrations of STPP are considered undesirable for environmental reasons, specifically, phosphates can lead to eutrophication in the environment. Therefore, there is a need to lower the usage of STPP in the production of detergent bars, including laundry bars.

Polycarboxylates have been found to be an alternative to STPP. Though polycarboxylates are good anti-redeposition and sequestration agents, their uses in laundry bars have been limited as it is regarded that additional liquid will make it difficult to form laundry bars by extrusion. WO 00/040691 discloses a phosphate-free laundry bar composition which incorporates polycarboxylates into the composition. The problem with WO 00/040691, however is that the reference does not disclose laundry detergents that are free of phosphates but merely discloses those that are "substantially free."

Accordingly, the need remains for a non-soap detergent bars having acceptable in-use wear rates, hardness, durability, rapid drying, low smear and that are more ecofriendly.

The present invention provides a non-soap detergent bar, comprising: a detergent surfactant; a builder; a psyllium; a cellulose derivative, wherein the cellulose derivative is selected from the group consisting of a hydroxyalkyl alkyl cellulose; a filler, wherein the filler includes sodium silicate; and water; wherein the non-soap detergent bar is a solid.

The present invention provides a method of making a non-soap detergent bar, comprising: providing a detergent surfactant; providing a builder; providing a psyllium; providing a cellulose derivative selected from the group consisting of a hydroxyalkyl alkyl cellulose; providing a filler, wherein the filler includes sodium silicate; and providing water; mixing the detergent surfactant, the builder, the psyllium, cellulose derivative, the filler and the water to form a combination; milling the combination; and extruding the milled combination to provide the non-soap detergent bar.

The present invention provides a method of making a non-soap detergent bar, comprising: providing a detergent surfactant; providing a builder; providing a psyllium; providing a cellulose derivative selected from the group consisting of a hydroxyalkyl alkyl cellulose; providing a filler, wherein the filler includes sodium silicate; providing a fragrance; providing a colorant and providing water; mixing the detergent surfactant, the builder, the psyllium, cellulose derivative, the filler, the fragrance, the colorant and the water to form a combination; milling the combination; and extruding the milled combination to provide the non-soap detergent bar.

DETAILED DESCRIPTION

We have surprisingly found that non-soap detergent bars containing a synergistic combination of sodium silicate, psyllium and a cellulose derivative selected from the group consisting of hydroxyalkyl alkyl cellulose facilitate high water content (>10 wt %) in the finished non-soap detergent bar while exhibiting enhanced wear resistance (preferably, wherein the finished non-soap detergent bar exhibits long term water retention and wherein the finished soap bar resists cracking from water loss for up to one year).

Unless otherwise indicated, ratios, percentages, parts, and the like are by weight.

As used herein, unless otherwise indicated, the terms "weight average molecular weight" and "Mw" are used interchangeably to refer to the weight average molecular weight as measured in a conventional manner with gel permeation chromatography (GPC) and conventional standards, such as polyethylene glycol standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Weight average molecular weights are reported herein in units of Daltons.

Preferably, the non-soap detergent bar of the present invention, comprises: a detergent surfactant (preferably, 5 to 30 wt % (more preferably, 7 to 25 wt %; still more preferably, 8 to 20 wt %; most preferably, 10 to 15 wt %), based on weight of the non-soap detergent bar, of the detergent surfactant); a builder (preferably, 8 to 50 wt % (more preferably, 9 to 40 wt %; still more preferably, 10 to 30 wt %; most preferably, 10.5 to 15 wt %), based on weight of the non-soap detergent bar, of the builder); a psyllium (preferably, 0.1 to 5 wt % (more preferably, 0.5 to 4 wt %; still more preferably, 0.75 to 3.5 wt %; most preferably, 1 to 3 wt %), based on weight of the non-soap detergent bar, of the psyllium); a cellulose derivative (preferably, 0.01 to 5 wt % (more preferably, 0.5 to 4 wt %; still more preferably, 0.6 to 3.5 wt %; most preferably, 0.65 to 3 wt %), based on weight of the non-soap detergent bar, of the cellulose derivative), wherein the cellulose derivative is selected from the group consisting of a hydroxyalkyl alkyl cellulose (e.g., hydroxyethyl methyl cellulose); a filler (preferably, 20 to 70 wt % (more preferably, 30 to 65 wt %; still more preferably, 40 to 60 wt %; most preferably, 45 to 55 wt %), based on weight of the non-soap detergent bar, of the filler), wherein the filler includes sodium silicate; and water (preferably, >10 to 30 wt % (more preferably, 12 to 28 wt %; still more preferably, 15 to 25 wt %; most preferably, 18 to 22 wt %), based on weight of the non-soap detergent bar, of the water); wherein the non-soap detergent bar is a solid (i.e., wherein the non-soap detergent bar does not perceptibly change shape when placed on a rigid surface and left to stand at room temperature, 22° C., and pressure, 101.4 kPa, for 24 hours)(preferably, wherein the non-soap detergent bar has at least one of the following properties an acceptable in-use wear rate, hardness, durability, rapid drying, low smear and improved eco-friendliness).

Preferably, the non-soap detergent bar of the present invention 5 to 30 wt % (preferably, 7 to 25 wt %; more preferably, 8 to 20 wt %; most preferably, 10 to 15 wt %), based on weight of the non-soap detergent bar, of a detergent surfactant. More preferably, the non-soap detergent bar of the present invention 5 to 30 wt % (preferably, 7 to 25 wt %; more preferably, 8 to 20 wt %; most preferably, 10 to 15 wt %), based on weight of the non-soap detergent bar, of a detergent surfactant; wherein the detergent surfactant is selected from the group consisting of alkyl sulfonic acids, alkyl sulfates, alkyl sulfonates, alkyl benzene sulfonic acid, alkyl benzene sulfates, alkyl benzene sulfonates, alkyl ether sulfonic acids, alkyl ether sulfates, alkyl ether sulfonates, paraffin sulfonic acids, paraffin sulfates, paraffin sulfonates, olefin sulfonic acids, olefin sulfates, olefin sulfonates, alpha-sulfocarboxylates, esters of alpha-sulfocarboxylates, alkyl glyceryl ether sulfonic acids, alkyl glyceryl ether sulfates, alkyl glyceryl ether sulfonates, sulfates of fatty acids, sulfonates of fatty acids, sulfonates of fatty acid esters, alkyl phenol polyethoxy ether sulfates, 2-acryloxy-alkane-1-sulfonic acid, 2-acryloxy-alkane-1-sulfonate, beta-alkyloxy alkane sulfonic acid, beta-alkyloxy alkane sulfonate, salts thereof and mixtures thereof. Still more preferably, the non-soap detergent bar of the present invention 5 to 30 wt % (preferably, 7 to 25 wt %; more preferably, 8 to 20 wt %; most preferably, 10 to 15 wt %), based on weight of the non-soap detergent bar, of a detergent surfactant; wherein the detergent surfactant is selected from the group consisting of $C_{8-20}$ alkyl benzene sulfonic acid, $C_{8-20}$ alkyl benzene sulfates, $C_{8-20}$ alkyl benzene sulfonate, $C_{8-20}$ alkyl ether sulfonic acids, $C_{8-20}$ alkyl ether sulfates, $C_{8-20}$ alkyl ether sulfonates, paraffin sulfonic acid, paraffin sulfates, paraffin sulfonate, alpha-olefin sulfonic acid, alpha-olefin sulfate, alpha-olefin sulfonate, sulfonates of fatty acids, sulfonates of fatty acid esters, salts thereof and mixtures thereof. Yet still more preferably, the non-soap detergent bar of the present invention 5 to 30 wt % (preferably, 7 to 25 wt %; more preferably, 8 to 20 wt %; most preferably, 10 to 15 wt %), based on weight of the non-soap detergent bar, of a detergent surfactant; wherein the detergent surfactant is selected from the group consisting of $C_{10-16}$ alkyl benzene sulfonic acid, $C_{10-16}$ alkyl benzene sulfonate, $C_{10-16}$ alkyl polyethoxy sulfonic acids, $C_{10-16}$ alkyl polyethoxy sulfates, $C_{10-16}$ alkyl polyethoxy sulfonates, salts thereof and mixtures thereof. Even more preferably, the non-soap detergent bar of the present invention 5 to 30 wt % (preferably, 7 to 25 wt %; more preferably, 8 to 20 wt %; most preferably, 10 to 15 wt %), based on weight of the non-soap detergent bar, of a detergent surfactant; wherein the detergent surfactant is selected from the group consisting of $C_{11-14}$ alkyl benzene sulfonic acid, $C_{11-14}$ alkyl benzene sulfonate, $C_{11-14}$ alkyl polyethoxy sulfonic acids, $C_{11-14}$ alkyl polyethoxy sulfates, $C_{11-14}$ alkyl polyethoxy sulfonates, salts thereof and mixtures thereof. Most preferably, the non-soap detergent bar of the present invention 5 to 30 wt % (preferably, 7 to 25 wt %; more preferably, 8 to 20 wt %; most preferably, 10 to 15 wt %), based on weight of the non-soap detergent bar, of a detergent surfactant; wherein the anionic surfactant includes (preferably, is) $C_{11-14}$ alkyl benzene sulfonic acid.

Preferably, the non-soap detergent bar of the present invention, comprises 8 to 50 wt % (preferably, 9 to 40 wt %; more preferably, 10 to 30 wt %; most preferably, 10.5 to 15 wt %), based on weight of the non-soap detergent bar, of the builder. More preferably, the non-soap detergent bar of the present invention, comprises 8 to 50 wt % (preferably, 9 to 40 wt %; more preferably, 10 to 30 wt %; most preferably, 10.5 to 15 wt %), based on weight of the non-soap detergent bar, of the builder; wherein the builder is selected from the group consisting of hydratable alkali metal phosphates, alkalis (including carbonates and bicarbonates), zeolites, ethylenediaminetetraacetate, nitrilotriacetate and mixtures thereof. More preferably, the non-soap detergent bar of the present invention, comprises 8 to 50 wt % (preferably, 9 to 40 wt %; more preferably, 10 to 30 wt %; most preferably, 10.5 to 15 wt %), based on weight of the non-soap detergent bar, of the builder; wherein the builder is selected from the group consisting of zeolite, sodium citrate, sodium silicate, sodium carbonate, calcium carbonate, sodium bicarbonate, calcium bicarbonate and mixtures thereof. Most preferably, the non-soap detergent bar of the present invention, comprises 8 to 50 wt % (preferably, 9 to 40 wt %; more preferably, 10 to 30 wt %; most preferably, 10.5 to 15 wt %), based on weight of the non-soap detergent bar, of the builder; wherein the builder includes at least one of sodium carbonate and calcium carbonate.

Preferably, the non-soap detergent bar of the present invention, comprises: (0.1 to 5 wt % (preferably, 0.5 to 4 wt %; more preferably, 0.75 to 3.5 wt %; most preferably, 1 to 3 wt %), based on weight of the non-soap detergent bar, of a psyllium. Psyllium is commercially available as particles or in powder form. Psyllium is preferably branched, mainly consisting of a neutral arabinoxylan with (1→4) and (1→3) xylopyranose backbones; wherein the side chains are composed of arabinose and xylose, which are connected to the main chain by β-3 and/or β-2 linkages. Psyllium is preferably extracted from the seed coat (husk or hull) of ispaghula or psyllium seeds of the *Plantago* genus. Psyllium is preferably composed mainly of arabinose (22 wt %), xylose (57 wt %) and uronic acids (10-15 wt %) with small amounts of galactose, rhamnose, glucose and mannose. Psyllium is preferably a highly branched acidic arabinoxylan with a high molecular weight (~1,500,000 Daltons).

Preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose. More preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose is selected from the group consisting of hydroxy-($C_{1-4}$)alkyl $C_{1-4}$ alkyl cellulose. Still more preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose is selected from the group consisting of hydroxyethyl methyl cellulose, hydroxypropyl methyl cellulose and mixtures thereof. Most preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose is hydroxyethyl methyl cellulose.

Preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose has a weight average molecular weight, $M_w$, of 25,000 to 4,000,000 Daltons (preferably, 25,000 to 1,500,000 Daltons; more preferably, 25,000 to 500,000 Daltons; most preferably, 25,000 to 150,000 Daltons). More preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose has a weight average molecular weight, $M_w$, of 25,000 to 4,000,000 Daltons (preferably, 25,000 to 1,500,000 Daltons; more preferably, 25,000 to 500,000 Daltons; most preferably, 25,000 to 150,000 Daltons); and wherein the hydroxyalkyl alkyl cellulose is selected from hydroxyethyl methyl cellulose, hydroxypropyl methyl cellulose and mixtures thereof. Most preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose has a weight average molecular weight, $M_w$, of 25,000 to 4,000,000 Daltons (preferably, 25,000 to 1,500,000 Daltons; more preferably, 25,000 to 500,000 Daltons; most preferably, 25,000 to 150,000 Daltons); and wherein the hydroxyalkyl alkyl cellulose is hydroxyethyl methyl cellulose.

Preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose is a cellulose ether having alkyl and hydroxyalkyl derivatives in which the average number of substituent groups per anhydroglucose unit is from 1 to 3 (preferably, 1.5 to 3; more preferably, 2 to 3). Preferably, the hydroxyalkyl groups have 1 to 4 carbon atoms (preferably, 1 to 3 carbon atoms; more preferably, 2 to 3 carbon atoms; most preferably, 2 carbon atoms). Preferably, the alkyl groups have 1 to 4 carbon atoms (preferably, 1 to 3 carbon atoms; more preferably, 1 to 2 carbon atoms; most preferably, 1 carbon atom).

Preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose has a substantially linear cellulose backbone. The term "substantially linear" as used herein and in the appended claims means that 97 to 100 wt % (preferably, 99 to 100 wt %) of all glucose units in the hydroxyalkyl alkyl cellulose are in a main chain of the cellulose backbone.

Preferably, the non-soap detergent bar of the present invention, comprises: 0.01 to 5 wt % (preferably, 0.5 to 4 wt %; more preferably, 0.6 to 3.5 wt %; most preferably, 0.65 to 3 wt %), based on weight of the non-soap detergent bar, of a cellulose derivative selected from the group consisting of a hydroxyalkyl alkyl cellulose; wherein the hydroxyalkyl alkyl cellulose has a substantially β-1,4 linked backbone. The term "substantially β-1,4 linked backbone" as used herein and in the appended claims means that 97 to 100 wt % (preferably, 99 to 100 wt %) of the glucose units in the hydroxyalkyl alkyl cellulose are bounded together with β-1,4 linkages. When less than 100 wt % of the glucose units are bounded together with β-1,4 linkages, the remaining glucose units may be bounded in a variety of ways, including, for example, β-1,2; β-1,3; β-1,6; β-2,3; α-1,2; α-1,3; α-1,4; α-1,6 and α-2,3 linkages and mixtures thereof.

Preferably, the non-soap detergent bar of the present invention, comprises a blend of the psyllium and the cellulose derivative at a weight ration of 1:9 to 9:1 (preferably, 1:5 to 5:1; more preferably, 1:4 to 4:1).

Preferably, the non-soap detergent bar of the present invention, comprises 20 to 70 wt % (preferably, 30 to 65 wt %; more preferably, 40 to 60 wt %; most preferably, 45 to 55 wt %), based on weight of the non-soap detergent bar, of a filler; wherein the filler includes sodium silicate. More preferably, the non-soap detergent bar of the present invention, comprises 20 to 70 wt % (preferably, 30 to 65 wt %; more preferably, 40 to 60 wt %; most preferably, 45 to 55 wt %), based on weight of the non-soap detergent bar, of a filler; wherein the filler further includes a substance selected from the group consisting of a sulfate, a chloride, a calcite, a silicate, a dolomite and mixtures thereof. Most preferably, the non-soap detergent bar of the present invention, comprises 20 to 70 wt % (preferably, 30 to 65 wt %; more preferably, 40 to 60 wt %; most preferably, 45 to 55 wt %), based on weight of the non-soap detergent bar, of a filler; wherein the filler comprises a mixture of magnesium sulfate, hydrated aluminum silicate (China clay), calcite, dolomite, sodium silicate and sodium chloride.

Preferably, the non-soap detergent bar of the present invention, comprises: >10 to 30 wt % (preferably, 12 to 28 wt %; more preferably, 15 to 25 wt %; most preferably, 18 to 22 wt %), based on weight of the non-soap detergent bar, of water. More preferably, the non-soap detergent bar of the present invention, comprises: >10 to 30 wt % (preferably, 12 to 28 wt %; more preferably, 15 to 25 wt %; most preferably, 18 to 22 wt %), based on weight of the non-soap detergent bar, of water; wherein the water is at least one of distilled and deionized water. Most preferably, the non-soap detergent bar of the present invention, comprises: >10 to 30 wt % (preferably, 12 to 28 wt %; more preferably, 15 to 25 wt %; most preferably, 18 to 22 wt %), based on weight of the non-soap detergent bar, of water; wherein the water is deionized water.

Preferably, the non-soap detergent bar of the present invention, is a solid. The term "solid" as used herein and in the appended claims in reference to a non-soap detergent bar means that the non-soap detergent bar will not perceptible change shape when placed on a rigid surface and left to stand on the rigid surface at room temperature (22° C.) and pressure (101.4 kPa) for 24 hours.

Preferably, the non-soap detergent bar of the present invention has a wear rate of 0.5 to 9 wt % (more preferably, 1 to 8 wt %), wherein the wear rate is the loss in weight of the non-soap detergent bar after 4 days of use.

Preferably, the non-soap detergent bar of the present invention, further comprises an optional ingredient. More preferably, the non-soap detergent bar of the present invention, further comprises an optional ingredient; wherein the optional ingredient is selected from the group consisting of humectants; processing aids (e.g., titanium dioxide); preservatives (e.g., benzoic acid, sorbic acid, phenoxyethanol); antioxidants (e.g., butylated hydroxytoluene); viscosity modifiers; polymers; free fatty acids; foam stabilizers; foam enhancers; chelating agents; antimicrobial agents (e.g., biocides); pH adjusting agents; pH buffering agents; fragrances/perfumes; colorants (e.g., dyes) and mixtures thereof. Most preferably, the non-soap detergent bar of the present invention, further comprises an optional ingredient selected from the group consisting of a fragrance, a colorant and mixtures thereof.

Preferably, the non-soap detergent bar of the present invention, further comprises a humectant. More preferably, the non-soap detergent bar of the present invention, further comprises 0.1 to 5 wt % (preferably, 0.25 to 2 wt %; more preferably, 0.5 to 1.5 wt %; most preferably, 0.75 to 1.25 wt %), based on weight of the non-soap detergent bar, of a humectant. Still more preferably, the non-soap detergent bar of the present invention, further comprises 0.1 to 5 wt % (preferably, 0.25 to 2 wt %; more preferably, 0.5 to 1.5 wt %; most preferably, 0.75 to 1.25 wt %), based on weight of the non-soap detergent bar, of a humectant; wherein the humectant is a polyhydric alcohol selected from the group consisting of glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose and mixtures thereof. Yet more preferably, the non-soap detergent bar of the present invention, further comprises 0.1 to 5 wt % (preferably, 0.25 to 2 wt %; more preferably, 0.5 to 1.5 wt %; most preferably, 0.75 to 1.25 wt %), based on weight of the non-soap detergent bar, of a humectant; wherein the humectant includes glycerin. Most preferably, the non-soap detergent bar of the present invention, further comprises 0.1 to 5 wt % (preferably, 0.25 to 2 wt %; more preferably, 0.5 to 1.5 wt %; most preferably, 0.75 to 1.25 wt %), based on weight of the non-soap detergent bar, of a humectant; wherein the humectant is glycerin.

Preferably, the non-soap detergent bar of the present invention, further comprises a processing aid. More preferably, the non-soap detergent bar of the present invention, further comprises 0.05 to 2 wt % (preferably, 0.1 to 1.5 wt %; more preferably, 0.25 to 1.25 wt %; most preferably, 0.5 to 1 wt %), based on weight of the non-soap detergent bar, of a processing aid. Still more preferably, the non-soap detergent bar of the present invention, further comprises: 0.05 to 2 wt % (preferably, 0.1 to 1.5 wt %; more preferably, 0.25 to 1.25 wt %; most preferably, 0.5 to 1 wt %), based on weight of the non-soap detergent bar, of a processing aid; wherein the processing aid is an inorganic powdery material selected from the group consisting of talc, calcite, kaolin, silicon dioxide, titanium dioxide, diatomaceous earth and mixtures thereof. Yet more preferably, the non-soap detergent bar of the present invention, further comprises: 0.05 to 2 wt % (preferably, 0.1 to 1.5 wt %; more preferably, 0.25 to 1.25 wt %; most preferably, 0.5 to 1 wt %), based on weight of the non-soap detergent bar, of a processing aid; wherein the processing aid is selected from the group consisting of talc, calcite, titanium dioxide and mixtures thereof. Most preferably, the non-soap detergent bar of the present invention, further comprises: 0.05 to 2 wt % (preferably, 0.1 to 1.5 wt %; more preferably, 0.25 to 1.25 wt %; most preferably, 0.5 to 1 wt %), based on weight of the non-soap detergent bar, of a processing aid; wherein the processing aid includes titanium dioxide.

Preferably, the non-soap detergent bar of the present invention, further comprises a chelating agent. More preferably, the non-soap detergent bar of the present invention, further comprises: 0.01 to 0.5 wt % (preferably, 0.05 to 0.3 wt %; more preferably, 0.075 to 0.25 wt %; most preferably, 0.1 to 0.2 wt %), based on weight of the non-soap detergent bar, of a chelating agent. Still more preferably, the non-soap detergent bar of the present invention, further comprises: 0.01 to 0.5 wt % (preferably, 0.05 to 0.3 wt %; more preferably, 0.075 to 0.25 wt %; most preferably, 0.1 to 0.2 wt %), based on weight of the non-soap detergent bar, of a chelating agent; wherein the chelating agent is selected from the group consisting of diethylenetriamine pentaacetic acid; 1-hydroxyethane 1,1-diphosphonic acid; citric acid; ethylene diamine tetraacetic acid (EDTA), salts thereof and mixtures thereof. Yet more preferably, the non-soap detergent bar of the present invention, further comprises: 0.01 to 0.5 wt % (preferably, 0.05 to 0.3 wt %; more preferably, 0.075 to 0.25 wt %; most preferably, 0.1 to 0.2 wt %), based on weight of the non-soap detergent bar, of a chelating agent; wherein the chelating agent is selected from the group consisting of diethylenetriamine pentaacetic acid pentasodium salt, 1-hydroxyethane 1,1-diphosphonic acid disodium salt; citric acid, ethylene diamine tetraacetic acid (EDTA), ethylene diamine tetraacetic acid tetrasodium salt and mixtures thereof. Most preferably, the non-soap detergent bar of the present invention, further comprises: 0.01 to 0.5 wt % (preferably, 0.05 to 0.3 wt %; more preferably, 0.075 to 0.25 wt %; most preferably, 0.1 to 0.2 wt %), based on weight of the non-soap detergent bar, of a chelating agent; wherein the chelating agent includes ethylene diamine tetraacetic acid tetrasodium salt.

Preferably, the non-soap detergent bar of the present invention, further comprises a fragrance. More preferably, the soap bar of the present invention, further comprises 0.01 to 3 wt % (preferably, 0.02 to 2 wt %; more preferably, 0.03 to 1 wt %; most preferably, 0.035 to 0.1 wt %), based on weight of the non-soap detergent bar, of a fragrance.

Preferably, the non-soap detergent bar of the present invention, further comprises a colorant. More preferably, the non-soap detergent bar of the present invention, further comprises: 0.01 to 3 wt % (preferably, 0.02 to 2 wt %; more preferably, 0.03 to 1 wt %; most preferably, 0.035 to 0.1 wt %), based on weight of the non-soap detergent bar, of a colorant.

Preferably, the non-soap detergent bar of the present invention is selected from a personal care bar, a dish bar and a laundry. More preferably, the non-soap detergent bar of the present invention is selected from a dish bar and a laundry bar. Most preferably, the non-soap detergent bar of the present invention is a laundry bar.

Preferably, the method of making a non-soap detergent bar of the present invention comprises: providing a detergent surfactant; providing a builder; providing a psyllium; providing a cellulose derivative selected from the group consisting of a hydroxyalkyl alkyl cellulose; providing a filler; providing water; mixing the detergent surfactant, the builder, the psyllium, the cellulose derivative, the filler and the water to form a combination (preferably, heating the detergent surfactant, the builder, the psyllium, the cellulose derivative, while mixing to form the combination); milling the combination; extruding the milled combination; and stamping the extruded material to provide the non-soap detergent bar. More preferably, the method of making a non-soap detergent bar of the present invention, comprises: providing a detergent surfactant; providing a builder; providing a psyllium; providing a cellulose derivative selected from the group consisting of a hydroxyalkyl alkyl cellulose (preferable, wherein the hydroxyalkyl alkyl cellulose is at least one of hydroxyethyl methyl cellulose and hydroxypropyl methyl cellulose); providing a filler; providing water; mixing the detergent surfactant, the builder, the psyllium, the cellulose derivative, the filler and the water to form a combination (preferably, heating the detergent surfactant, the builder, the psyllium, the cellulose derivative, while mixing to form the combination); milling the combination; extruding the milled combination; and stamping the extruded material to provide the non-soap detergent bar.

Some embodiments of the present invention will now be described in detail in the following Examples.

Comparative Example C and Examples 1-2: Non-Soap Detergent Bars

Non-soap detergent bars are prepared having the composition noted in TABLE 1 for each of Comparative Example C and Examples 1-2. The ingredients are mixed together in the amounts noted in TABLE 1 in a sigma mixer. All ingredients are added sequentially with no specific order, except for the perfume, which is added last. The entire mass is then transferred from the sigma mixer to a triple roll mill to triturate the mixture. All the processes are carried out under ambient conditions in a laboratory. The mass received from roll mill is then plodded in a screw plodder and extruded at a temperature of 45 to 55° C. The extruded mass is then cut into small pieces to provide a final product non-soap detergent bar.

TABLE 1

| | Example (wt %) | | |
|---|---|---|---|
| Ingredient | C | 1 | 2 |
| Sodium carbonate | 10.00 | 7.81 | 7.81 |
| Magnesium sulphate | 1.00 | 0.78 | 0.78 |
| Colorant (blue) | 0.05 | 0.04 | 0.04 |
| Aqueous linear $C_{11-14}$ alkyl benzene sulfonic acid (90 wt %) | 16.85 | 16.00 | 16.00 |
| Whitening agent[1] | 0.05 | 0.04 | 0.04 |
| Hydrated aluminum silicate | 15.00 | 11.71 | 11.71 |
| Calcite | 22.00 | 17.18 | 17.18 |
| Dolomite | 25.00 | 19.52 | 19.52 |
| Sodium silicate | 4.50 | 3.51 | 3.51 |
| Sodium tripolyphosphate (STPP, $Na_5P_3O_{10}$) | 6.00 | — | — |
| Perfume | 0.11 | 0.16 | 0.16 |
| Hydroxyethyl methyl cellulose[2] | — | 2.00 | — |
| Hydroxyethyl methyl cellulose[3] | — | — | 2.00 |
| Psyllium | — | 2.00 | 2.00 |
| Deionized water | q.s. | q.s. | q.s. |

[1]Tinopal CBSX fluorescent whitening agent available from BASF
[2]Walocel MW 60000 PFV hydroxyethyl methyl cellulose available from The Dow Chemical Company
[3]Walocel MKX 60000 PF01 hydroxyethyl methyl cellulose available from The Dow Chemical Company

We claim:

1. A non-soap detergent bar, comprising:
 a detergent surfactant;
 a builder;
 a psyllium;
 a cellulose derivative, wherein the cellulose derivative is selected from the group consisting of a hydroxyalkyl alkyl cellulose;
 a filler, wherein the filler includes sodium silicate;
 water;
 wherein the non-soap detergent bar is a solid;
 wherein the weight ratio of the psyllium to the hydroxyalkyl alkyl cellulose is 1:9 to 9:1.

2. The non-soap detergent bar of claim 1, wherein the non-soap detergent bar includes:
 5 to 30 wt %, based on weight of the non-soap detergent bar, of the detergent surfactant;
 8 to 50 wt %, based on weight of the non-soap detergent bar, of the builder;
 0.1 to 5 wt %, based on weight of the non-soap detergent bar, of the psyllium;
 0.01 to 5 wt %, based on weight of the non-soap detergent bar, of the cellulose derivative, wherein the cellulose derivative is selected from the group consisting of a hydroxyethyl methyl cellulose, a hydroxypropyl methyl cellulose and mixtures thereof;
 20 to 70 wt %, based on weight of the non-soap detergent bar, of the filler; and
 >10 to 30 wt %, based on weight of the non-soap detergent bar, of the water.

3. The non-soap detergent bar of claim 2, wherein the cellulose derivative is hydroxyethyl methyl cellulose.

4. The non-soap detergent bar of claim 2, further comprising 0.01 to 3 wt %, based on weight of the non-soap detergent bar, of a colorant.

5. The non-soap detergent bar of claim 4, further comprising 0.01 to 3 wt %, based on weight of the non-soap detergent bar, of a fragrance.

6. The non-soap detergent bar of claim 5, wherein the filler further includes at least one of magnesium sulfate, hydrated aluminum silicate, calcite, dolomite and sodium chloride.

7. The non-soap detergent bar of claim 5, wherein the filler further includes a mixture of magnesium sulfate, hydrated aluminum silicate, calcite, dolomite and sodium chloride.

8. The non-soap detergent bar of claim 7, wherein the non-soap detergent bar is a laundry bar.

9. The non-soap detergent bar of claim 1, wherein the non-soap detergent bar includes:
 8 to 20 wt %, based on weight of the non-soap detergent bar, of the detergent surfactant;
 10 to 30 wt %, based on weight of the non-soap detergent bar, of the builder;
 0.75 to 3.5 wt %, based on weight of the non-soap detergent bar, of the psyllium;
 0.60 to 3.5 wt %, based on weight of the non-soap detergent bar, of the cellulose derivative, wherein the cellulose derivative is selected from the group consisting of a hydroxyethyl methyl cellulose, a hydroxypropyl methyl cellulose and mixtures thereof;
 40 to 60 wt %, based on weight of the non-soap detergent bar, of the filler; and
 15 to 25 wt %, based on weight of the non-soap detergent bar, of the water.

10. The non-soap detergent bar of claim 1, wherein the non-soap detergent bar includes:
 10 to 15 wt %, based on weight of the non-soap detergent bar, of the detergent surfactant;
 10.5 to 15 wt %, based on weight of the non-soap detergent bar, of the builder;
 1 to 3 wt %, based on weight of the non-soap detergent bar, of the psyllium;
 0.65 to 3 wt %, based on weight of the non-soap detergent bar, of the cellulose derivative, wherein the cellulose derivative is selected from the group consisting of a hydroxyethyl methyl cellulose, a hydroxypropyl methyl cellulose and mixtures thereof;
 45 to 55 wt %, based on weight of the non-soap detergent bar, of the filler; and
 18 to 22 wt %, based on weight of the non-soap detergent bar, of the water.

11. The non-soap detergent bar of claim 10, further comprising
 0.01 to 3 wt %, based on weight of the non-soap detergent bar, of a colorant;
 0.01 to 3 wt %, based on weight of the non-soap detergent bar, of a fragrance;

wherein the cellulose derivative is hydroxyethyl methyl cellulose; and
wherein the filler further includes at least one of magnesium sulfate, hydrated aluminum silicate, calcite, dolomite and sodium chloride.

12. The non-soap detergent bar of claim 11, wherein the filler further includes a mixture of magnesium sulfate, hydrated aluminum silicate, calcite, dolomite and sodium chloride.

13. The non-soap detergent bar of claim 12, wherein the non-soap detergent bar is a laundry bar.

14. A method of making a non-soap detergent bar according to claim 1, comprising:
providing a detergent surfactant;
providing a builder;
providing a psyllium;
providing a cellulose derivative selected from the group consisting of a hydroxyalkyl alkyl cellulose;
providing a filler, wherein the filler includes sodium silicate; and
providing water;
mixing the detergent surfactant, the builder, the psyllium, cellulose derivative, the filler and the water to form a combination;
milling the combination; and
extruding the milled combination to provide the non-soap detergent bar.

15. The method of claim 14, further comprising:
providing a fragrance; and
providing a colorant;
wherein the fragrance and the colorant are mixed along with the detergent surfactant, the builder, the psyllium, cellulose derivative, the filler and the water to form the combination.

16. A non-soap detergent bar, consisting of:
a detergent surfactant, wherein the detergent surfactant is selected from the group consisting of alkyl sulfonic acids, alkyl sulfates, alkyl sulfonates, alkyl benzene sulfonic acid, alkyl benzene sulfates, alkyl benzene sulfonates, alkyl ether sulfonic acids, alkyl ether sulfates, alkyl ether sulfonates, paraffin sulfonic acids, paraffin sulfates, paraffin sulfonates, olefin sulfonic acids, olefin sulfates, olefin sulfonates, alpha-sulfocarboxylates, esters of alpha-sulfocarboxylates, alkyl glyceryl ether sulfonic acids, alkyl glyceryl ether sulfates, alkyl glyceryl ether sulfonates, sulfates of fatty acids, sulfonates of fatty acids, sulfonates of fatty acid esters, alkyl phenol polyethoxy ether sulfates, 2-acryloxy-alkane-1-sulfonic acid, 2-acryloxy-alkane-1-sulfonate, beta-alkyloxy alkane sulfonic acid, beta-alkyloxy alkane sulfonate, salts thereof and mixtures thereof;
a builder, wherein the builder is selected from the group consisting of hydratable alkali metal phosphates, alkalis, zeolites, ethylenediaminetetraacetate, nitrilotriacetate and mixtures thereof;
a psyllium;
a cellulose derivative, wherein the cellulose derivative is selected from the group consisting of a hydroxy-($C_{1-4}$) alkyl $C_{1-4}$ alkyl cellulose;
a filler, wherein the filler is a mixture of sodium silicate, magnesium sulfate, hydrated aluminum silicate, calcite, dolomite and sodium chloride;
water; and
an optional ingredient; wherein the optional ingredient is selected from the group consisting of a humectant; a processing aid; a preservative; an antioxidant; a chelating agent; a fragrance/perfume; a colorant and mixtures thereof;
wherein the humectant is selected from the group consisting of glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose and mixtures thereof;
wherein the processing aid is selected from the group consisting of talc, calcite, kaolin, silicon dioxide, titanium dioxide, diatomaceous earth and mixtures thereof;
wherein the preservatives are selected from the group consisting of benzoic acid, sorbic acid, phenoxyethanol and mixtures thereof;
wherein the antioxidant is butylated hydroxytoluene;
wherein the chelating agent is selected from the group consisting of diethylenetriamine pentaacetic acid; 1-hydroxyethane 1,1-diphosphonic acid; citric acid; ethylene diamine tetraacetic acid (EDTA), salts thereof and mixtures thereof; and
wherein the non-soap detergent bar is a solid.

17. The non-soap detergent bar of claim 16, wherein the non-soap detergent bar consists of
8 to 20 wt %, based on weight of the non-soap detergent bar, of the detergent surfactant;
10 to 30 wt %, based on weight of the non-soap detergent bar, of the builder;
0.75 to 3.5 wt %, based on weight of the non-soap detergent bar, of the psyllium;
0.6 to 3.5 wt %, based on weight of the non-soap detergent bar, of the cellulose derivative;
40 to 60 wt %, based on weight of the non-soap detergent bar, of the filler; and
15 to 25 wt %, based on weight of the non-soap detergent bar, of water;
wherein the weight ratio of the psyllium to the hydroxyalkyl alkyl cellulose is 1:9 to 9:1.

18. The non-soap detergent bar of claim 16, wherein the non-soap detergent bar consists of
10 to 15 wt %, based on weight of the non-soap detergent bar, of the detergent surfactant;
10.5 to 15 wt %, based on weight of the non-soap detergent bar, of the builder;
1 to 3 wt %, based on weight of the non-soap detergent bar, of the psyllium;
0.65 to 3 wt %, based on weight of the non-soap detergent bar, of the cellulose derivative;
45 to 55 wt %, based on weight of the non-soap detergent bar, of the filler; and
18 to 22 wt %, based on weight of the non-soap detergent bar, of water;
wherein the weight ratio of the psyllium to the hydroxylakyl alkyl cellulose is 1:5 to 5:1.

19. The non-soap detergent bar of claim 18,
wherein the detergent surfactant is a $C_{11-14}$ alkyl benzene sulfonic acid;
wherein the builder is sodium carbonate and calcium carbonate;
wherein the cellulose derivative is a hydroxyethyl methyl cellulose;
wherein the humectant is glycerine;
wherein the processing aid is titanium dioxide; and
wherein the chelating agent is selected from the group consisting of diethylenetriamine pentaacetic acid pentasodium salt, 1-hydroxyethane 1,1-diphosphonic acid disodium salt; citric acid, ethylene diamine tetraacetic acid (EDTA), ethylene diamine tetraacetic acid tetrasodium salt and mixtures thereof.

20. The non-soap detergent bar of claim 18,
wherein the detergent surfactant is a $C_{11-14}$ alkyl benzene sulfonic acid;
wherein the builder is sodium carbonate and calcium carbonate;
wherein the cellulose derivative is a hydroxyethyl methyl cellulose;
wherein the humectant is glycerine;
wherein the processing aid is titanium dioxide;
wherein the chelating agent is ethylene diamine tetraacetic acid; and
wherein the weight ratio of the psyllium to the hydroxyalkyl alkyl cellulose is 1:4 to 4:1.

\* \* \* \* \*